US009956416B2

(12) United States Patent
Ghosh et al.

(10) Patent No.: US 9,956,416 B2
(45) Date of Patent: May 1, 2018

(54) MONITORING ACTIVATION TIMES FOR USE IN DETERMINING PACING EFFECTIVENESS (71) Applicant: Medtronic, Inc., Minneapolis, MN (US)

(72) Inventors: Subham Ghosh, Circle Pines, MN (US); Robert W Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 520 days.

(21) Appl. No.: 13/706,472

(22) Filed: Dec. 6, 2012

(65) Prior Publication Data

US 2013/0165983 A1 Jun. 27, 2013

Related U.S. Application Data (60) Provisional application No. 61/579,473, filed on Dec. 22, 2011.

(51) Int. Cl.
*A61N 1/37* (2006.01)
*A61N 1/39* (2006.01)
*A61N 1/362* (2006.01)
*A61N 1/368* (2006.01)

(52) U.S. Cl.
CPC ......... *A61N 1/3706* (2013.01); *A61N 1/3622* (2013.01); *A61N 1/3627* (2013.01); *A61N 1/3682* (2013.01); *A61N 1/3937* (2013.01)

(58) Field of Classification Search
None
See application file for complete search history.

(56) References Cited

U.S. PATENT DOCUMENTS

| 4,374,382 | A | 2/1983 | Markowitz |
| 5,117,824 | A | 6/1992 | Keimel et al. |
| 5,545,186 | A | 8/1996 | Olson et al. |
| 5,755,736 | A | 5/1998 | Gillberg et al. |
| 6,381,493 | B1 * | 4/2002 | Stadler et al. .......... 607/9 |
| 6,393,316 | B1 | 5/2002 | Gillberg et al. |
| 7,286,876 | B2 | 10/2007 | Yonce et al. |
| 7,664,550 | B2 | 2/2010 | Eick et al. |
| 7,912,544 | B1 | 3/2011 | Min et al. |
| 8,160,700 | B1 * | 4/2012 | Ryu et al. .......... 607/9 |

(Continued)

FOREIGN PATENT DOCUMENTS

| EP | 2 016 976 A1 | 1/2009 |
| EP | 2 188 011 B1 | 5/2011 |

(Continued)

OTHER PUBLICATIONS (PCT/US2012/070541) PCT Notification of Transmittal of the International Search Report and the Written Opinion of the International Searching Authority.

(Continued)

*Primary Examiner* — Michael Kahelin (57) ABSTRACT

Methods and/or devices may be configured to track effectiveness of pacing therapy by monitoring activation times over time, e.g., between pacing stimulus and electrical activity resulting from the pacing stimulus. Generally, the methods and/or devices may determine whether the delivered pacing therapy was effective based on the measured activation times.

2 Claims, 6 Drawing Sheets (56) References Cited

U.S. PATENT DOCUMENTS

| | | |
|---|---|---|
| 2004/0220635 A1 | 11/2004 | Burnes |
| 2005/0131478 A1* | 6/2005 | Kim et al. ............... 607/27 |
| 2006/0224198 A1 | 10/2006 | Dong et al. |
| 2009/0005832 A1 | 1/2009 | Zhu et al. |
| 2009/0270937 A1 | 10/2009 | Yonce et al. |
| 2009/0318995 A1 | 12/2009 | Keel et al. |
| 2011/0022112 A1 | 1/2011 | Min |
| 2011/0054559 A1 | 3/2011 | Rosenberg et al. |
| 2011/0054560 A1 | 3/2011 | Rosenberg et al. |
| 2012/0185012 A1* | 7/2012 | Ryu et al. ............... 607/25 |

FOREIGN PATENT DOCUMENTS

| | | |
|---|---|---|
| EP | 2 349 468 A1 | 8/2011 |
| WO | 2005/056108 A2 | 6/2005 |
| WO | 2010/039501 A1 | 4/2010 |

OTHER PUBLICATIONS

Hayes et al., "Cardiac Resynchronization Therapy and the Relationship of Percent Biventricular Pacing to Symptoms and Survival," *Heart Rhythm*, Sep. 2011; 8(9):1469-1475.

Kamath et al, "The Utility of 12-Lead Holter Monitoring in Patients with Permanent Atrial Fibrillation for the Identification of Nonresponders After Cardiac Resynchronization Therapy," *Journal of the American College of Cardiology*, Mar. 24, 2009; 53(12): 1050-1055.

Steinhaus BM., "Estimating Cardiac Transmembrane Activation and Recovery Times from Unipolar and Bipolar Extracellular Electrograms: A Simulation Study," *Circulation Research*, 1989, 64:449-462.

* cited by examiner

MONITORING ACTIVATION TIMES FOR USE IN DETERMINING PACING EFFECTIVENESS

CROSS-REFERENCE TO RELATED APPLICATIONS

This application claims the benefit of U.S. Provisional Application No. 61/579,473, filed on Dec. 22, 2011. The disclosure of the above application is incorporated herein by reference in its entirety.

BACKGROUND OF THE INVENTION

The disclosure herein relates to methods and devices for monitoring activation time within cardiac tissue to determine whether pacing therapy was effective and/or to maintain effective pacing therapy.

Implantable medical devices (IMD) are capable of utilizing pacing therapies, such as cardiac resynchronization therapy (CRT), to maintain hemodynamic benefits to patients. Pacing therapy may be delivered from an implantable generator, through a lead, and into the patient's heart. Basic programmable pacing parameters include pacing amplitude, pacing rate, pulse duration, and pacing pathway or vector (e.g., bipolar such as a lead tip electrode to a lead ring electrode, etc. or unipolar such as a lead tip electrode to IMD casing, or housing), which all may be configured to ensure effective therapy to the patient.

Retention of effective pacing (e.g., left ventricular pacing) may be beneficial in CRT. A common cause for ineffective pacing may be loss of capture due to, e.g., lead dislodgement, extracardiac stimulation, exit block, pacing from a suboptimal location, etc. Current devices may temporarily suspend, or interrupt, pacing therapy for one or more heart beats to determine if one or more pacing electrodes are effectively capturing cardiac tissue for delivery of pacing therapy. In other words, the pacing therapy is periodically interrupted to determine if effective pacing is being delivered. For example, a left ventricular (LV) capture management routine for a device employing left ventricular or biventricular pacing may involve comparison of two measured times while pacing therapy has been temporarily ceased or suspended (e.g., interrupted). The first time may be measured between a left ventricular (LV) pace and the electrical activity sensed at a right ventricular (RV) electrode with respect to the LV pace. The second time may be measured between a right atrial (RA) pace and the electrical activity sensed at a RV electrode with respect to the RA pace. The device may detect capture, or loss of capture, by comparing the first time to the second time. For example, if the second time, i.e., the RA pace to the RV sense, is less than the first time, i.e., the LV pace to the RV sense, then it may be determined that the LV pacing is ineffective.

SUMMARY

Generally, diagnostic methods and devices that can perform a beat-to-beat monitoring of effective pacing, without interruption of pacing therapy, are described herein. For example, exemplary devices and methods described herein relate to monitoring one or more activation times and determining whether pacing therapy was effective based on the one or more monitored activation times. More specifically, exemplary devices and methods may monitor activation times between delivering pacing stimulus using a pacing electrode and sense electrical activity resulting from the stimulus using a sensing electrode. These monitored activation times may be analyzed to determine whether pacing therapy is effective (or compromised/ineffective).

In at least one embodiment, exemplary methods and/or systems may utilize a multipolar lead including additional electrodes other than pacing electrodes (e.g., the lead may include electrodes other than used for pacing) where electrogram (EGM) data and timings can be monitored beat-to-beat. Effectiveness of pacing (e.g., LV pacing) may be monitored beat-by-beat based on measurements of activation times (e.g., differences between activation times over time) measured using the additional non-pacing electrodes. For example, if activation times increase over time, then pacing may have become ineffective.

One exemplary implantable medical device for tracking effectiveness of pacing therapy to a patient may include at least a therapy delivery module, a sensing module, and a control module coupled to both the therapy delivery module and the sensing module. The therapy delivery module may be configured to deliver pacing therapy to a patient's heart using at least a first electrode (e.g., configured to pace the left ventricle, or any other portion, of the patient's heart), and the sensing module may be configured to sense electrical activity of the patient's heart using a second electrode (e.g., an electrode not used for pacing, a far-field electrode, a defibrillation coil, etc.) during the delivery of pacing therapy using at least the first electrode. In at least one embodiment, the first electrode and the second electrode are located on the same lead. The control module may be configured to measure an activation time for each of the plurality of heart beats between the delivery of a pacing stimulus of the pacing therapy using the first electrode and a selected fiducial point of the sensed electrical activity (e.g., a peak, a change, a change in slope, a zero crossing, and/or any other statistically relevant fiducial point within the sensed electrical activity) resulting from the delivered pacing stimulus of the pacing therapy. The control module may be further configured to determine whether the delivered pacing therapy was effective based on the measured activation times.

One exemplary method of tracking effectiveness of pacing therapy provided using an implantable medical device may include delivering pacing therapy to a patient's heart using at least a first electrode (e.g., a pacing electrode configured to pace the left ventricle) of the implantable medical device. The pacing therapy may be delivered over a plurality of heart beats. The exemplary method may further include sensing electrical activity of the patient's heart using at least a second electrode (e.g., a sensing electrode not used for pacing, a far-field electrode, a defibrillation coil, etc.) of the implantable medical device during the delivery of the pacing therapy using at least the first electrode and measuring an activation time for each of the plurality of heart beats between the delivery of a pacing stimulus of the pacing therapy using the first electrode and a selected fiducial point of the sensed electrical activity (e.g., a peak, a change, a peak in slope/derivative, a change in slope/derivative, a zero crossing, a threshold crossing, etc. of the sensed electrical activity) resulting from the delivered pacing stimulus of the pacing therapy. The exemplary method may further include determining whether the delivered pacing therapy was effective based on the measured activation times.

In one or more embodiments of the devices and methods described herein, to determine whether the delivered pacing therapy was effective, the control modules may be further configured to and the methods may further calculate an activation time difference between the measured activation time and a reference activation time and determine that the delivered pacing therapy was ineffective if the activation time difference falls outside of a selected range (e.g., the range may be selected based on known effective pacing therapy). The reference activation time may be measured between the delivery of the pacing stimulus of the pacing therapy using the first electrode and the selected fiducial point of the sensed electrical activity during known effective pacing therapy. In at least one embodiment, to determine that the delivered pacing therapy was ineffective, it may be determined that the delivered pacing therapy is ineffective if the activation time difference falls outside of a selected range for a first selected number of heart beats out of a second selected number of heart beats.

In one or more embodiments of the devices and methods described herein, the control modules may be further configured to and the methods may further include initiating an alert if it is determined that the delivered pacing therapy was ineffective and/or adjusting one or more pacing parameters if it is determined that the delivered pacing therapy was ineffective.

In one or more embodiments of the devices and methods described herein, the control modules may be further configured to and the methods may further include classifying the measured activation time as being characteristic of one of a plurality of types of pacing therapy (e.g., biventricular pacing, left ventricle only pacing, right ventricle only pacing, etc.) and an intrinsic activation, and determining that the delivered pacing therapy was ineffective if the classification is not the same as the pacing therapy programmed to be delivered.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-6. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 1:
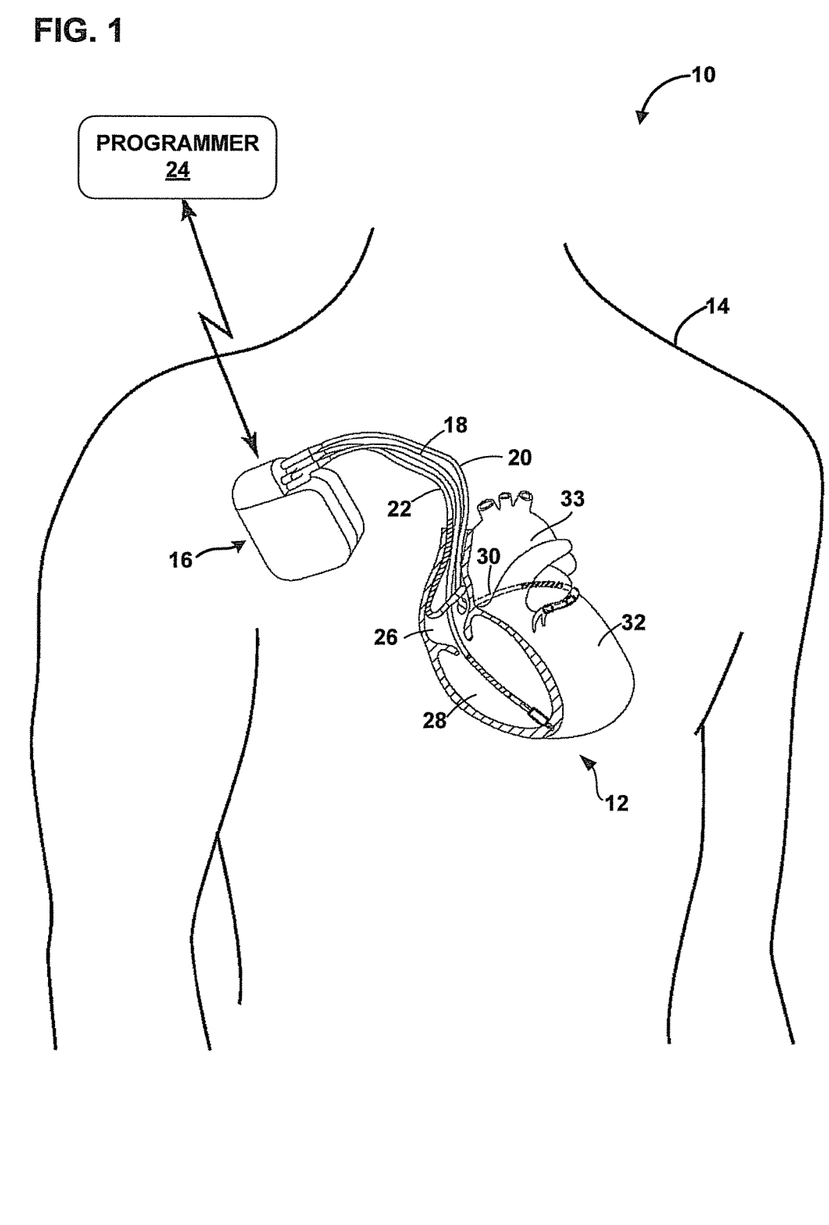
FIG. 1 is a diagram of an exemplary system including an exemplary implantable medical device (IMD).

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
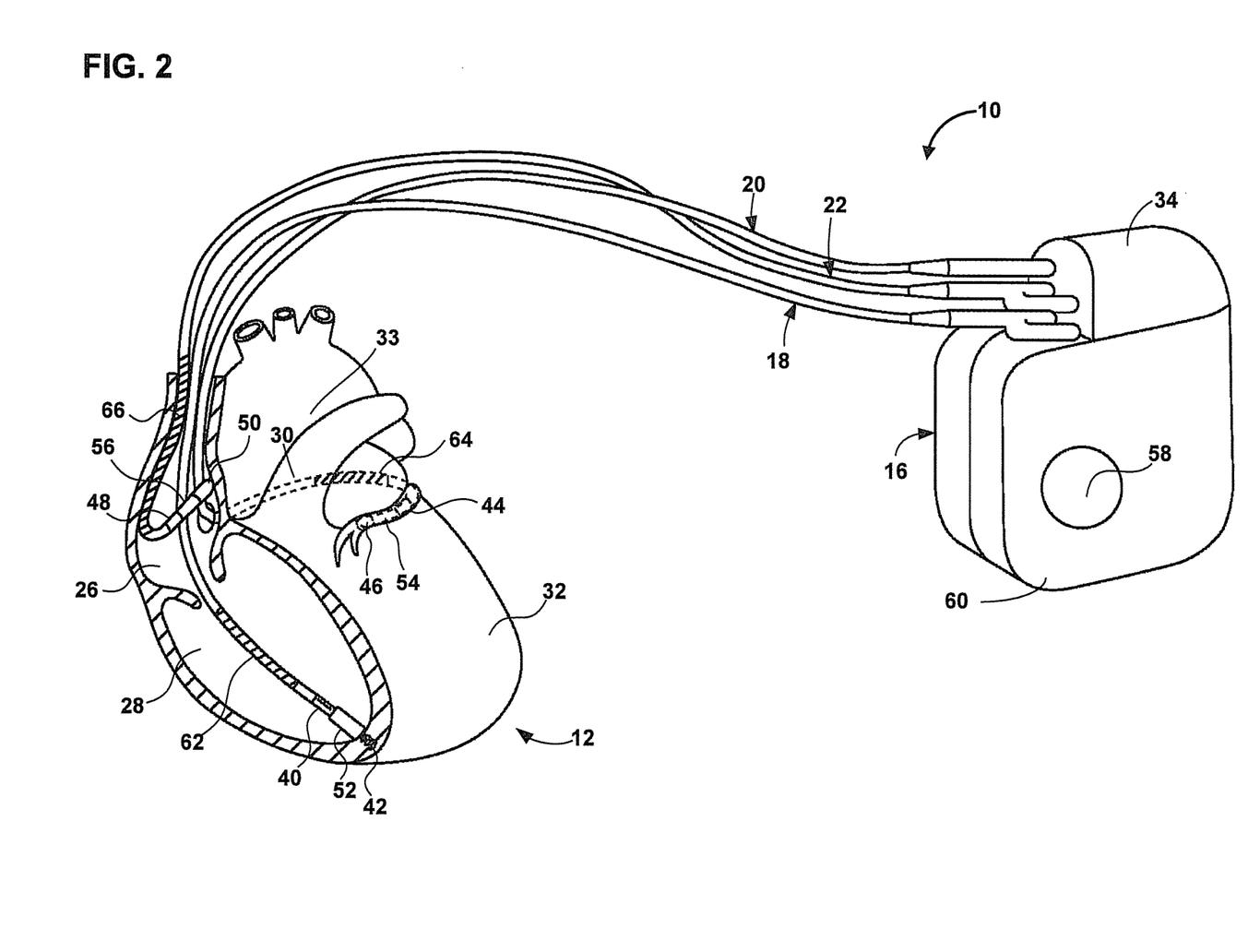
FIG. 2 is a diagram of the exemplary IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendible helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48 and 50 may be used for unipolar sensing or pacing in combination with housing electrode 58. Further, any of electrodes 40, 42, 44, 46, 48, 50, 58, which are not being used to deliver pacing therapy, may be used to sense electrical activity during pacing therapy (e.g., for use in determining activation times). As described in further detail with reference to FIG. 3, the housing 60 may enclose a therapy delivery module that may include a stimulation generator for generating cardiac pacing pulses and defibrillation or cardioversion shocks, as well as a sensing module for monitoring the patient's heart rhythm.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in determining activation times). In at least one embodiment, the LV elongated electrode 64 may be used to sense electrical activity of a patient's heart during the deliver of pacing therapy.

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3:
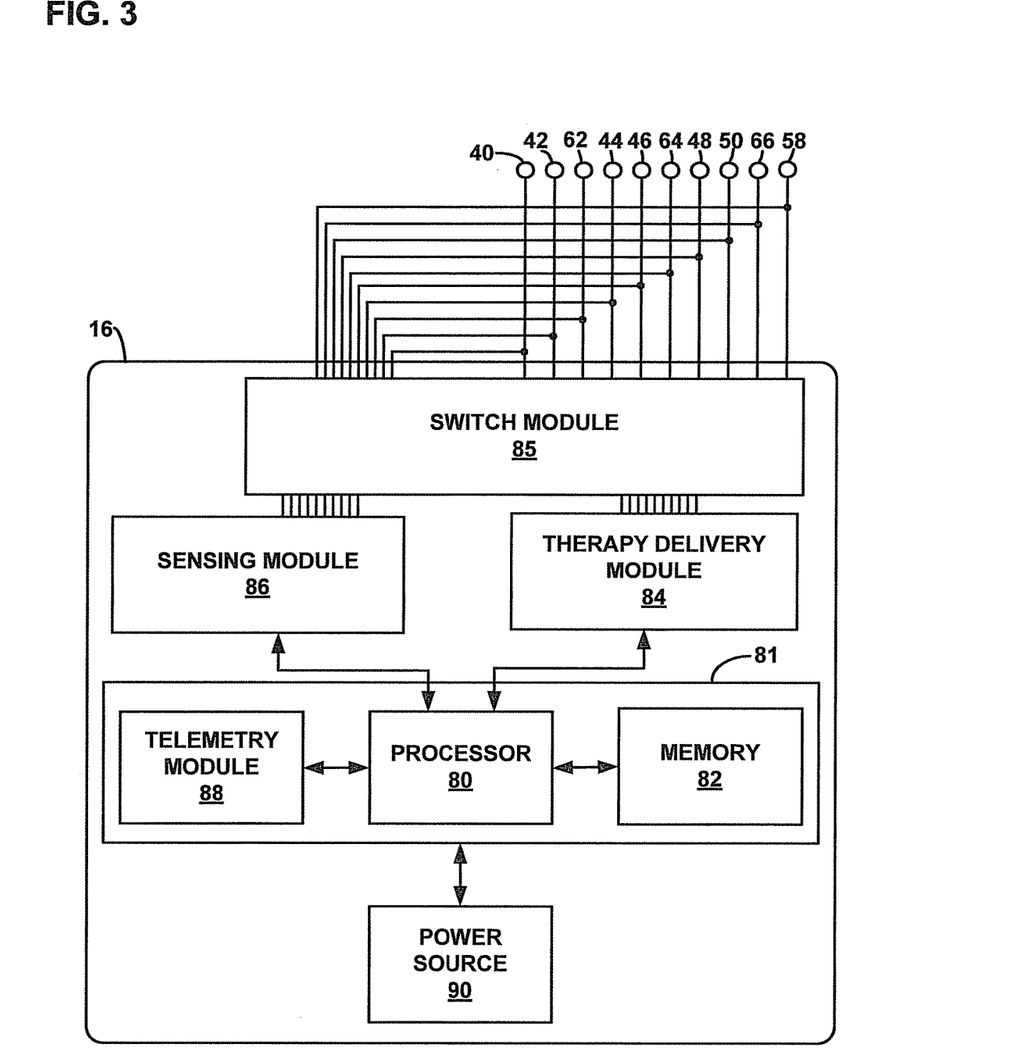
FIG. 3 is a block diagram of an exemplary IMD, e.g., the IMD of FIGS. 1-2.

FIG. 3 is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart. In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to detect and classify the patient's heart rhythm from the electrical signals. For example, the processor 80 may be configured to measure activation times of cardiac tissue using EGMs from one or more electrodes in contact, or in proximity, with cardiac tissue by employing any of the numerous signal processing methodologies known in the art.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Activation times of cardiac tissue during pacing (e.g., LV only pacing or during biventricular pacing) measured at one or more non-pacing electrodes (e.g., on the same or a different lead) may be used to determine whether the pacing was effective. For example, if a pacing electrode configured to deliver pacing becomes less effective (e.g., due to dislodgement, extracardiac stimulation, etc.), the activation time across cardiac tissue resulting from the pacing electrode may change. Further, the degree of fusion of paced and intrinsic wavefronts (e.g., when a paced event in which intrinsic ventricular activation fuses, or merges, with paced ventricular activation) may change if the speed of the intrinsic conduction of the atrioventricular node has changed.

Measurement of activation times can be performed by picking an appropriate fiducial point (e.g., peak values, minimum values, minimum slopes, maximum slopes, zero crossings, threshold crossings, etc. of a near or far-field EGM) and measuring time between the delivery of pacing stimulus using a pacing electrode and the appropriate fiducial point with the electrical activity sensed by a non-pacing electrode. In other words, activation times between a pacing electrode and a non-pacing electrode distant from the pacing electrode may be measured by picking, or selecting, an appropriate point within the EGM recorded by the non-pacing electrode during pacing therapy (e.g., biventricular stimulation, LV only pacing, etc.) with respect to the pacing spike.

The exemplary methods and/or devices described herein may track, or monitor, the effectiveness of pacing therapy by using cardiac activation times. One manifestation of the basic flow can be seen in exemplary method 100 of FIG. 4. Exemplary method 100 includes various processes to measure activation times and determine whether the activation times indicate that the pacing therapy was effective. Exemplary method 100 is intended to illustrate the general functional operation of the devices described herein, and should not be construed as reflective of a specific form of software or hardware necessary to practice all of the methods described herein. It is believed that the particular form of software will be determined primarily by the particular system architecture employed in the device (e.g., IMD 16) and by the particular detection and therapy delivery methodologies employed by the device and/or system. Providing software and/or hardware to accomplish the described methods in the context of any modern IMD, given the disclosure herein, is within the abilities of one of skill in the art.

Figure 4:
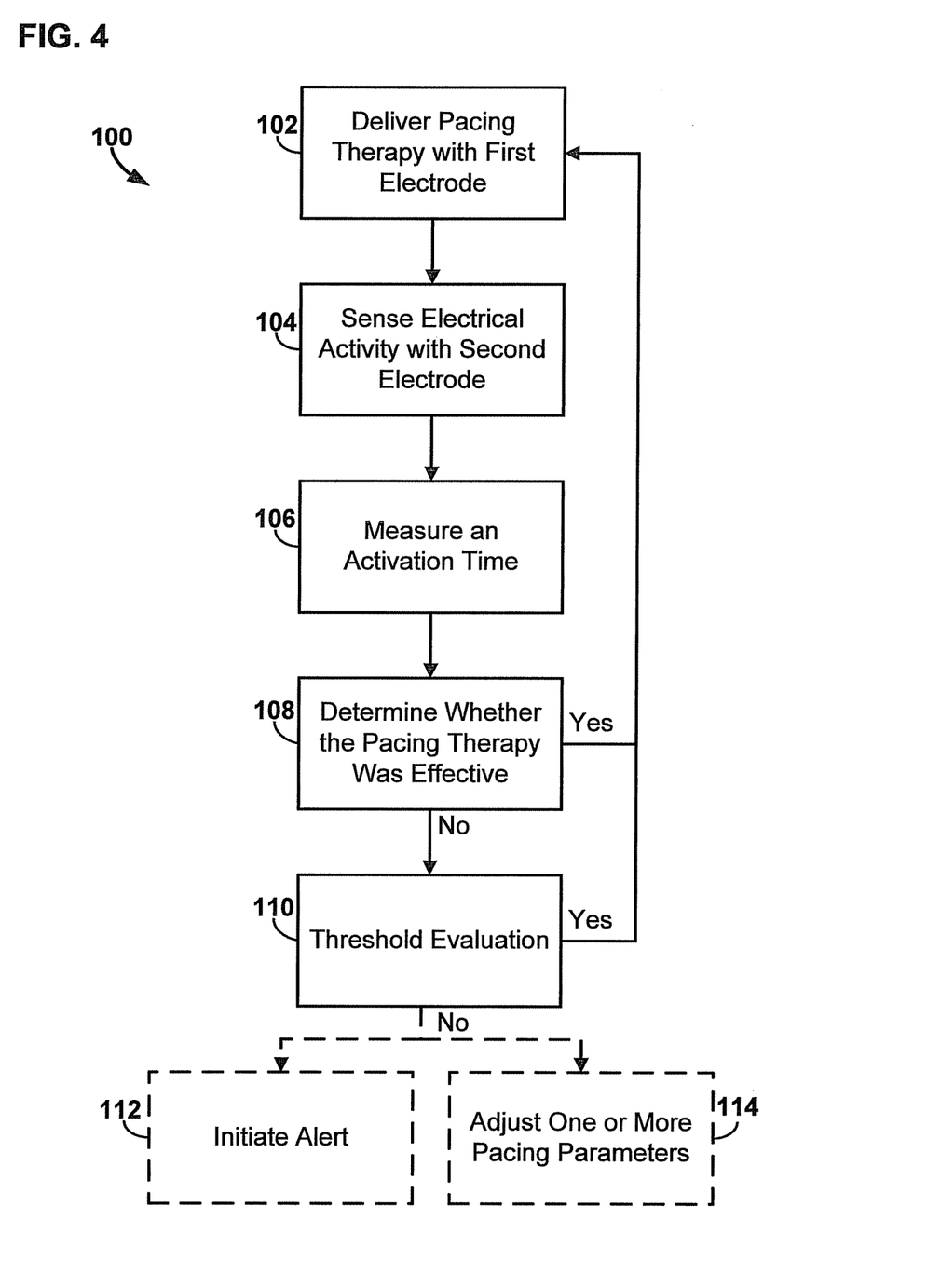
FIG. 4 is a general flow chart of an exemplary method for tracking effectiveness of pacing therapy, e.g., using the IMDs of FIGS. 1-3.

The exemplary method 100 of FIG. 4 includes delivering pacing therapy 102 (e.g., using the IMD 16 described herein). Delivering pacing therapy 102 may include monitoring a patient's heart and delivering electrical pacing pulses to the patient's heart, e.g., to maintain the patient's heart beat (e.g., to regulate a patient's heart beat, to improve and/or maintain a patient's hemodynamic efficiency, etc.)

As described herein, during the delivery of pacing therapy 102, the pacing therapy 102 may become less effective due to, e.g., lead dislodgement, exit block, extracardiac stimulation, ventricular ectopy, intrinsic rhythm interference with pacing, a change in cardiac substrate/tissue proximate the pacing electrode, changes in ventricular conduction velocity, changes in ventricular conduction patterns, changes in intrinsic AV delays, changes in heart rate, changes in sympathetic or parasympathetic stimulation, etc. Exemplary method 100 tracks the effectiveness of the pacing therapy by sensing electrical activity 104 of the patient's heart during the delivery of pacing therapy 102 with one or more electrodes not used to pace the patient's heart. For example, the electrical activity may be monitored using at least one sensing electrode during the delivery of pacing stimulus (e.g., pacing pulses) from one or more pacing electrodes such that the electrical activity which results from the pacing stimulus may be sensed, or seen, in the electrogram of the at least one sensing electrode. In other words, the electrical activity of the patient's heart may be monitored during a time period in which the electrical activity due to the pacing may be sensed.

In at least one embodiment, the pacing therapy may be delivered with at least a first electrode and the electrical activity may be sensed with at least a second electrode. As described herein, the second electrode, or the electrode configured to sense the electrical activity resulting from the pacing stimulus, may not be a pacing electrode. In other words, the second electrode may not be configured for delivering pacing therapy. For example, the second, or sensing, electrode may be a pacing electrode that is simply not being used to deliver pacing therapy (e.g., not ever used for delivery of pacing therapy, not being used to deliver pacing therapy at the same time as the first electrode, etc.). Further, for example, the second electrode may be a defibrillator electrode configured to deliver defibrillation therapy when needed.

Further, the second electrode may be located a distance away from the first electrode (e.g., the pacing electrode) such that an activation time may be monitored. For example, if the first electrode and the second electrode were located too close to one another, an activation time between the two may be too short for use in determining the effectiveness of the pacing therapy. In at least one embodiment, the pacing, or first electrode, may be a LV tip electrode configured to pace the free wall of the left ventricle, and the sensing electrode, or second electrode, may be LV ring electrode or a RV elongated (e.g., defibrillation) electrode.

Since the exemplary method 100 may not use pacing electrodes to sense the electrical activity for use in tracking effectiveness of the pacing therapy, the sensing 104 may take place for every paced beat (e.g., beat-to-beat, etc.) such that pacing therapy is not interrupted to track pacing effectiveness. As such, each heart beat of a plurality of heart beats may be monitored using exemplary method 100 without interruption.

An activation time may be measured 106 using the electrical activity sensed 104 using a sensing electrode. For example, a fiducial point on the waveform of the sensed electrical activity may be selected to be used with the exemplary method 100. The time between the delivery of the pacing therapy (e.g., to the LV) and the reception of the fiducial point within the waveform of the sensed electrical activity resulting form the pacing therapy (e.g., pacing stimulus) is the activation time.

The fiducial point may be selected to be a characteristic of the sensed electrical activity resulting from (e.g., a product of) the pacing therapy that is repeatable or consistently measurable such that, e.g., the measured activation times may be a reliable indicator of effectiveness. In at least one embodiment, the fiducial point may be a peak, or maximum, value in the waveform, or electrogram, sensed by the sensing electrode. In at least another embodiment, the fiducial point may be a zero crossing (e.g., across the x-axis) in the waveform sensed by the sensing electrode. In at least another embodiment, the fiducial point may be an initial spike in the waveform sensed by the sensing electrode.

Based on the measured activation time 106, the exemplary method 100 may determine whether the pacing therapy was effective 108 for that particular heart beat. For example, the measured activation time may be compared to a selected value (e.g., such as a reference activation time) indicative of effective pacing therapy. Further, for example, the measured activation time may be compared to a selected range of values indicative of effective pacing therapy. In other words, the measured activation time may fall within a range of effective activation times (e.g., which may indicate that the pacing therapy is effective) or may fall outside a range of effective activation times (e.g., which may indicate that the pacing therapy is ineffective).

In at least one embodiment, a plurality of activation times may be measured using a plurality of different sensing electrodes and/or pacing electrodes. Further, each of the plurality of activation times may be used to determine if the pacing therapy is effective. For example, the activation times for a plurality of sensing electrodes may define a pattern that may be classified as being indicative of effective or ineffective pacing. For instance, electrical activity, or activation, may be sensed at a first electrode, then at a second electrode 15 milliseconds after the first electrode, and then at a third electrode 30 milliseconds after the second electrode during effective pacing therapy. Therefore, if a different pattern is monitored using each of the first, second, and third electrodes, it may be indicate ineffective pacing.

In at least one embodiment, a reference activation time may be provided that is indicative of effective pacing therapy. For example, the reference activation time may be measured using the same pacing electrode and the same sensing electrode when the delivered pacing therapy is known to be effective. For instance, the reference activation time may be measured shortly after implantation of the pacing therapy device (e.g., IMD 16) while the patient is still under medical observation. In at least one embodiment, the reference activation time may be established while determining effective pacing therapy using a separate measurement instrument such as ultrasound, pressure sensors, impedance sensors, etc.

In at least another embodiment, an activation time difference may be calculated by subtracting the measured activation time from the reference activation time. In one or more embodiments, if the activation time difference exceeds a threshold value, it may be indicative of ineffective pacing therapy. Further, in one or more embodiments, if the activation time difference falls outside of a selected range, it may be indicative of ineffective pacing therapy.

In at least another embodiment, a mean value representative of a plurality of sensed activation times, and its variability, may be evaluated for a selected number of beats during a post-implant follow-up at physician's office with biventricular stimulation or LV only stimulation. A physician, or another practitioner, may visually monitor the pacing therapy using, e.g., an electrocardiogram of the patient's heart, to confirm that the pacing therapy is effective. The mean value of the sensed activation times may be used for a reference activation time indicative of effective pacing therapy. The variability may be used to calculate a range, or percentage difference, from the reference activation time that may be acceptable or allowable without indicating ineffective pacing therapy. A reference activation may be greater than or equal to about 10 milliseconds, about 15 milliseconds, about 20 milliseconds, about 30 milliseconds, about 40 milliseconds, about 50 milliseconds, about 70 milliseconds, about 100 milliseconds, etc. and/or less than or equal to about 110 milliseconds, about 125 milliseconds, about 150 milliseconds, about 175 milliseconds, about 200 milliseconds, about 225 milliseconds, about 250 milliseconds, etc. Further, an acceptable variability may be greater than or equal to about 5 milliseconds, about 7 milliseconds, about 10 milliseconds, about 15 milliseconds, etc. and/or less than or equal to about 20 milliseconds, about 25 milliseconds, about 30 milliseconds, about 40 milliseconds, about 50 milliseconds. In at least one embodiment, a reference activation time for biventricular pacing may be about 63 milliseconds (e.g., measured with a non-pacing electrode at a LV base while performing simultaneous biventricular stimulation from a LV mid electrode and a RV apical electrode) and the variability may be about +/−5 milliseconds for 100 paced beats. Such values may be different for each patient and each different electrode combination used for pacing and sensing.

If the pacing therapy is determined to be effective, the exemplary method 100 may continue delivering pacing therapy 102, sensing electrical activity 104, and measuring activation times 106 to, e.g., maintain pacing therapy and provide tracking effectiveness of the pacing therapy. If pacing therapy is determined to be ineffective, one or more actions may be taken. For example, as shown in FIG. 4, an alert, or alarm, may be initiated 112 to indicate to the patient or a technician that pacing may be ineffective (e.g., a warning sound or other perceptible signal that indicates to the patient that the patient should visit a physician for further investigation). Further, for example, as shown in FIG. 4, one or more pacing parameters may be adjusted 114 such as, e.g., pulse width, voltage, AV delay, VV delay, pacing location and/or vector, additional pacing, etc.

In certain situations, pacing therapy may be determined to be intermittently ineffective, and thus, any subsequent action such as initiating an alert 122 may not need to be triggered. For example, one or more leads may temporarily shift (e.g., due to patient movements, etc.), which may lead to extraordinary activation times. In such situations, it may be determined that the pacing therapy is not effective for one or more heart beats, but in subsequent heart beats, the pacing therapy may be determined to be effective once again. As such, the exemplary method 100 may further include a threshold evaluation process 110 to determine whether the pacing therapy is not effective over a selected number of heart beats. For example, if the pacing therapy was determined to be ineffective for 6 out of the past 8 heart beats, then process 110 may determine that the pacing therapy is truly ineffective. If the pacing therapy was determined to be ineffective for 2 out of the past 8 hearts beats, then process 110 may determine that the pacing therapy is still effective. In other words, the threshold may evaluate the effectiveness of the pacing therapy within a rolling window of heart beats, and if a selected number within the rolling window exceeds a threshold, it may be determined that the pacing therapy is not effective. Additionally, other metrics of pacing efficacy may be maintained.

In at least one embodiment, for any normal biventricular, or left ventricular only, paced beat (e.g., excluding tachycardia pacing) whose activation time falls beyond a range of allowable values (e.g., greater than a maximum activation time or less than a minimum activation time), an ineffective pacing counter may be incremented by 1. If 8 or more of the last 10 paced beats were ineffective, additional action such as, e.g., initiate an alarm/alert 112 indicating possible loss of pacing, may be triggered. In addition, an IMD delivering pacing therapy may keep track, or monitor, a BV or LV pacing ratio, which is the number of paced heart beats divided by the total number of heart beats. Using the exemplary methods and process described herein, the number of paced heart beats may be subtracted for each heart beat that the pacing therapy is determined to be ineffective thereby providing a pacing ratio that may be more accurate (e.g., since ineffective paced beats may be excluded from the ratio). In other words, an index of the proportion of effective paced beats, which is number of effective paced beats divided by the total number of paced beats, may be provided based on activation times.

As mentioned, if it is determined that the pacing therapy may be ineffective, the exemplary method 100 may initiate an alert 112 and/or adjust one or more pacing parameters 114. In at least one embodiment, initiating an alert 112 may include forcing a CARELINK transmission urging a clinic to follow-up with the patient and screen for lead dislodgement (e.g., LV lead dislodgement) or possible extracardiac stimulation. In at least one embodiment, adjusting one or more pacing parameters 114 may include increasing one or more parameters such as pacing voltage, which may be executed as part of a capture management process, e.g., to determine if pacing may still be effective at different parameters (e.g., pulse width, voltage, AV delay, VV delay, pacing location and/or vector, additional pacing, etc.).

Figure 5:
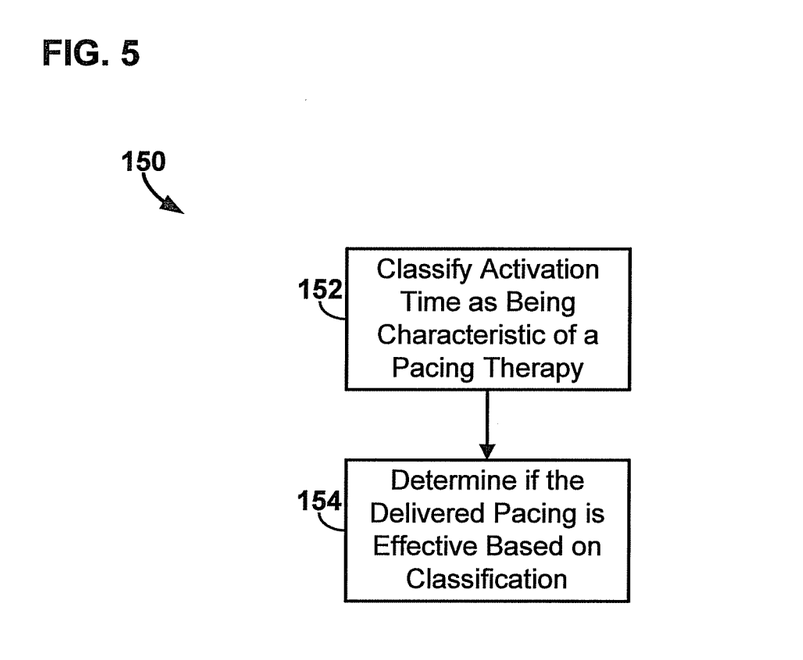
FIG. 5 is a flow chart of an exemplary method for use in classifying activation times.

An additional exemplary method 150 for using activation times to determine if pacing therapy is effective is depicted in FIG. 5. Generally, exemplary method 150 uses rhythm characterizations based on inter-electrode conduction delays, for example, to determine pacing effectiveness. For example, activation times may be indicative of a particular type of pacing therapy or intrinsic conduction. As such, sensed activation times may indicate what type of pacing therapy is being delivered or is not being delivered.

As such, exemplary method 150 may classify a sensed activation time 152 as being characteristic of one of a plurality of types of a pacing therapy or an intrinsic conduction. For example, intrinsic conduction (e.g., natural sinus rhythm (NSR)), right ventricular only pacing, left ventricular only pacing, and biventricular pacing may each have characteristic activation times. One or more sensed activation times may be compared to the characteristic activation times of the different types of pacing therapy or an intrinsic conduction, and then classified based on that comparison.

The activation times shown below in Table 1 were monitored in a patient using multi-polar lead along a coronary sinus branch. The activation times were gathered, or monitored, using either a LV apex electrode or a LV base electrode (e.g., an electrode more proximal than the LV apex electrode if located on the same multi-electrode lead) during delivery of pacing therapy (e.g., pacing stimulus) from a LV mid-wall electrode and a RV apical electrode.

TABLE 1

Activation Times Measured Using Different Electrodes for Different Pacing Therapies and Natural Sinus Rhythm

| Rhythm | LV apex electrode | LV base electrode |
|---|---|---|
| NSR | 59 +/− 4 | 17 +/− 3 |
| RV-p | 158 +/− 7 | 162 +/− 4 |
| LV-p | — +/− — | −75 +/− 2 |
| BiV-p | 5 +/− 2 | 63 +/− 5 |

Figure 6:
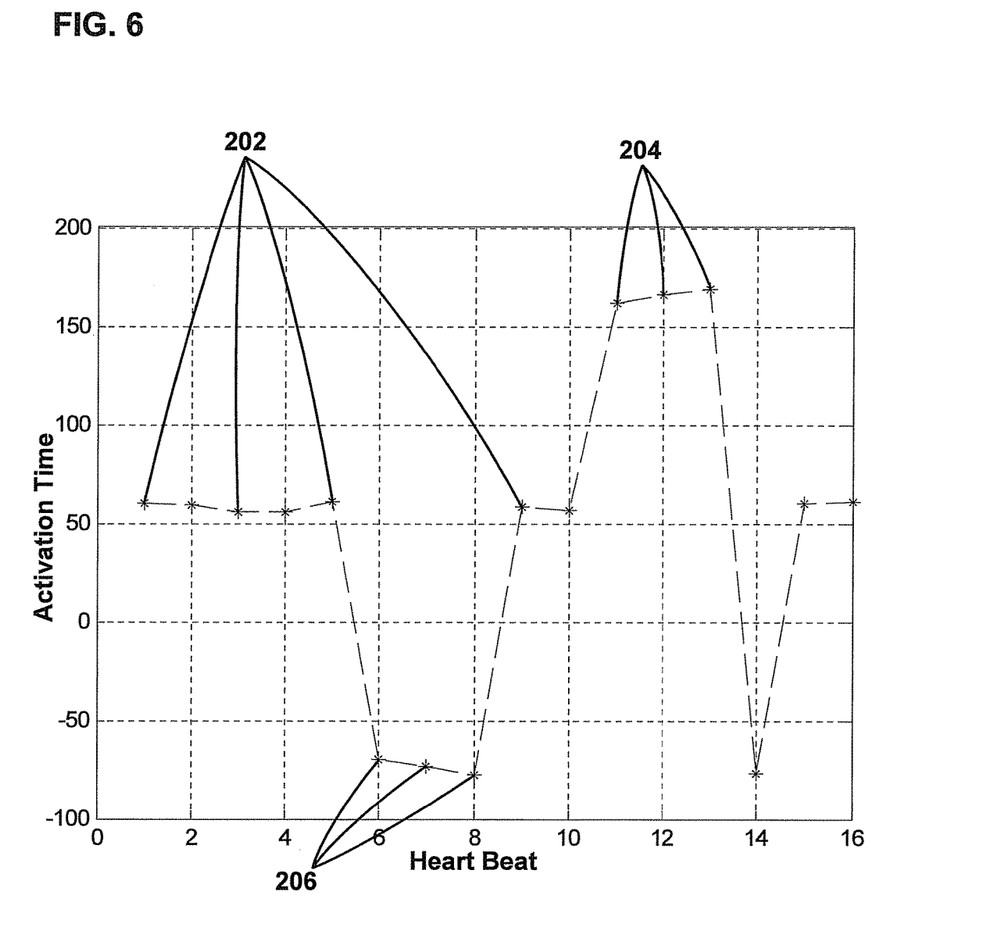
FIG. 6 graph depicting activation times resulting from different types of pacing therapy

As shown in Table 1, each pacing therapy or intrinsic conduction (NSR) has a characteristic activation time for each pair of electrodes. Thus, the type of therapy being delivered, or not delivered in the case of an intrinsic conduction, may be determined based on sensed activation time. For example, a plot of activation times versus heart beats is shown in FIG. 6. The activation times were monitored using a LV base electrode during delivery of pacing therapy from one or both of a LV mid-wall electrode and a RV apical electrode. As shown, the activation times 202 are characteristic of biventricular pacing, the activation times 204 are characteristic of right ventricular only pacing, and the activation times 206 are characteristic of left ventricular only pacing.

Since the pacing therapy type or intrinsic conduction may be determined through classification based on activation time 152, the exemplary method 150 may further determine if the delivered pacing therapy is effective based on the classification 154. More specifically, if the therapy programmed to be delivered, e.g., using the IMD 16, is different than (or not the same as) the classification, then the pacing therapy may be ineffective. For example, if the activation time is classified as being characteristic of LV only pacing, and BV pacing is being delivered, it may be determined that the RV pacing of the BV pacing may be ineffective. Further, for example, if the activation time is classified as being characteristic of RV only pacing, and BV pacing is being delivered, it may be determined that the LV pacing of the BV pacing may be ineffective.

In other words, if complete loss of LV capture occurs during biventricular resynchronization pacing, the activation times might look like RV only-pacing. If both LV and RV capture loss occurs, the activation times may look like normal sinus rhythm (NSR). If only RV capture loss occurs, the activation times may look more like LV only pacing (LV-p).

The results of such classifications may be tied to device action as well. For example, if activation times look like RV only pacing for a selected number of beats (e.g., indicating a complete loss of LV capture), then the exemplary methods and devices may try to step up, or increase, LV pacing output. Further, for example, if activation times that correspond only to LV only pacing are detected, then RV capture may be lost and the exemplary methods and device may initiate, or trigger, a RV capture management routine.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An implantable medical device for tracking effectiveness of pacing therapy to a patient comprising:
   a therapy delivery module configured to deliver pacing therapy to a patient's heart using at least a first electrode;
   a sensing module configured to sense electrical activity of the patient's heart using a second electrode during the delivery of pacing therapy using at least the first electrode; and
   a control module coupled to the therapy delivery module and to the sensing module and configured to:
   measure an activation time for each of a plurality of heart beats between the delivery of a pacing stimulus of the pacing therapy using the first electrode and a selected fiducial point of the sensed electrical activity resulting from the delivered pacing stimulus of the pacing therapy;
   determine beat-to-beat data representative of whether the pacing stimulus of the delivered pacing therapy for each heart beat of the plurality of heart beats was effective or ineffective based on the measured activation times, wherein the determination of whether the pacing stimulus of the delivered pacing therapy for each heart beat was effective or ineffective is indicative of whether capture occurred as a result of the delivered pacing stimulus; and
   use the beat-to-beat data to determine if the pacing therapy was effective or ineffective for the patient, wherein to use the beat-to-beat data to determine whether the delivered pacing therapy was effective or ineffective, the control module is further configured to:
   classify, for each heart beat, the measured activation time as being characteristic of one of a plurality of types of pacing therapy and an intrinsic activation; and
   determine that the delivered pacing therapy was ineffective if the classification is not the same as the pacing therapy programmed to be delivered.

2. A method of tracking effectiveness of pacing therapy provided using an implantable medical device, wherein the method comprises:
   delivering pacing therapy to a patient's heart using at least a first electrode of an implantable medical device, wherein the pacing therapy is delivered over a plurality of heart beats;
   sensing electrical activity of the patient's heart using at least a second electrode of the implantable medical device during the delivery of the pacing therapy using at least the first electrode;
   measuring an activation time for each of a plurality of heart beats between the delivery of a pacing stimulus of the pacing therapy using the first electrode and a selected fiducial point of the sensed electrical activity resulting from the delivered pacing stimulus of the pacing therapy;
   determining beat-to-beat data representative of whether the pacing stimulus of the delivered pacing therapy for each heart beat of the plurality of heart beats was effective or ineffective based on the measured activation times, wherein determination of whether the pacing stimulus of the delivered pacing therapy for each heart beat was effective or ineffective is indicative of whether capture occurred as a result of the delivered pacing stimulus; and using the beat-to-beat data to determine if the pacing therapy was effective or ineffective for the patient, wherein using the beat-to-beat data to determine whether the delivered pacing therapy was effective or ineffective for the patient comprises:

classifying, for each heart beat, the measured activation time as being characteristic of one of a plurality of types of pacing therapy and an intrinsic activation; and determining that the delivered pacing therapy was ineffective if the classification is not the same as the pacing therapy programmed to be delivered.

* * * * *